United States Patent
Drizen et al.

(10) Patent No.: US 6,387,407 B1
(45) Date of Patent: *May 14, 2002

(54) TOPICAL DRUG PREPARATIONS

(75) Inventors: Alan Drizen; Peter Rothbart, both of Ontario (CA); Gary M. Nath, Bethesda, MD (US)

(73) Assignee: L.A.M. Pharmaceutical Corporation, North York (CA)

(*) Notice: Subject to any disclaimer, the term of this patent is extended or adjusted under 35 U.S.C. 154(b) by 0 days.

This patent is subject to a terminal disclaimer.

(21) Appl. No.: 09/280,841

(22) Filed: Mar. 30, 1999

Related U.S. Application Data

(63) Continuation-in-part of application No. 08/536,750, filed on Sep. 29, 1995, now abandoned.

(51) Int. Cl.⁷ .......................... A61K 9/14; A01N 43/04
(52) U.S. Cl. ................... 424/488; 424/484; 424/486; 514/54; 514/825; 514/886; 514/887; 514/994
(58) Field of Search ................. 424/484, 485, 424/488; 514/54, 825, 886, 887, 944

(56) References Cited

U.S. PATENT DOCUMENTS

| | | |
|---|---|---|
| 4,127,118 A | 11/1978 | Latorre |
| 4,521,421 A | 6/1985 | Foreman |
| 4,636,524 A | 1/1987 | Balazs et al. |
| 4,801,587 A | 1/1989 | Voss et al. |
| 5,015,474 A | 5/1991 | Parnell |
| 5,017,229 A | 5/1991 | Burns et al. |
| 5,059,603 A | 10/1991 | Rubin |
| 5,118,510 A | 6/1992 | Kuhrts |
| 5,126,348 A | 6/1992 | McMurray |
| 5,143,724 A | 9/1992 | Leshchiner et al. |
| 5,190,962 A | 3/1993 | Barberich et al. |
| 5,190,967 A | 3/1993 | Riley |
| 5,246,702 A | 9/1993 | Vecchi |
| 5,256,652 A | 10/1993 | El-Rashidy |
| 5,278,192 A | 1/1994 | Fung et al. |
| 5,318,780 A | 6/1994 | Viegas et al. |
| 5,333,621 A | 8/1994 | Denzer |
| 5,346,935 A | 9/1994 | Suzuki et al. |
| 5,356,629 A | 10/1994 | Sander et al. |
| 5,380,757 A | 1/1995 | Horrobin |
| 5,380,758 A | 1/1995 | Stamler et al. |
| 5,399,581 A | 3/1995 | Laragh |
| 5,474,535 A | 12/1995 | Place et al. |
| 5,489,610 A | 2/1996 | Fung et al. |
| 5,518,732 A * | 5/1996 | Nigam ....................... 424/427 |
| 5,525,357 A | 6/1996 | Keefer et al. |
| 5,527,893 A | 6/1996 | Burns et al. |
| 5,565,466 A | 10/1996 | Gioco et al. |
| 5,583,144 A | 12/1996 | Kral |
| 5,679,394 A | 10/1997 | Long, Jr. et al. |
| 5,731,339 A | 3/1998 | Lowery |
| 5,741,511 A | 4/1998 | Lee et al. |
| 5,928,667 A * | 7/1999 | Rosenblatt et al. ......... 424/484 |
| 6,120,804 A * | 9/2000 | Drizen et al. ............... 424/488 |
| 6,251,436 B1 * | 6/2001 | Drizen et al. ............... 424/488 |

FOREIGN PATENT DOCUMENTS

| | | |
|---|---|---|
| EP | 0266968 | 10/1987 |
| EP | 0346297 | 5/1989 |
| EP | 0539627 | 10/1991 |
| EP | 0516026 | 5/1992 |
| EP | 516026 A1 * | 12/1992 |
| EP | 0581581 | 7/1993 |
| WO | WO 92/03141 | 3/1992 |
| WO | WO 93/00894 | 1/1993 |

OTHER PUBLICATIONS

Billmeyer. Textbook of Polymer Science. Interscience Publishers. New York, NY. 1962, see pp. 62–104.*

Kirk–Othmer. Encyclopedia of Chemical Technology, 2nd Ed. vol. 16, 1968, see pp. 242–253.*

Nakajima, "Fractionation of Linear Polyethylene with Gel Permeation Chromatography", Advances in Chemistry Series 125, Published by American Chemical Society, pp. 89–107 (1973).*

Allen et al., "Objective Double–blind Evaluation of Erectile Function with Intracorporeal Papaverine in Combination with Phentolamine and/or Prostaglandin E1", *The Journal of Urology*, 148:1181–83 (1992).

Bennett et al., "An Improved Vasoactive Drug Combination for Pharmcological Erection Program", *The Journal of Urology*, 146:1564–65 (1991).

Goldstein et al., "Oral Sildenafil in the Treatment of Erectile Dysfunction", *The New England Journal of Medicine*, vol. 338, No. 20:1397–1404 (1998).

Lakin et al., "Intracaverous Injection Therapy: Analysis of Results and Complications", *The Journal of Urology*, 143:1138–41 (1990).

Valdevenito et al., "Intracavernous Self–Injection Pharmacotherapy Program: Analysis of Results and Complications", *Int. J. Impotence Res.*, 6:81–91 (1994).

MUSE® (Alprostadil) (package insert), Vivu Inc. (1996).

* cited by examiner

*Primary Examiner*—Diana Dudash
*Assistant Examiner*—Gina Yu
(74) *Attorney, Agent, or Firm*—Nath & Associates PLLC; Gary M. Nath

(57) ABSTRACT

Topical gelled compositions comprising an optional drug dispersed within a polymer matrix, methods of producing the same and treatments with the complex.

6 Claims, No Drawings

TOPICAL DRUG PREPARATIONS

RELATED APPLICATIONS

This application is a continuation-in-part of U.S. patent application Ser. No. 08/536,750 filed Sep. 29, 1995 now abandoned, the entire contents of which are incorporated herein in their entirety.

FIELD OF THE INVENTION

This invention relates to the preparation of a transdermal delivery system. The preparation is designed to deliver therapeutic levels of a drug to specific sites below the dermal level of the skin including, but not limited to, knees, ankles, hands, feet and neck.

DESCRIPTION OF THE PRIOR ART

Over the years, methods have beer developed to achieve the efficient delivery of a therapeutic drug to a mammalian body part requiring pharmaceutical treatment. Use of an aqueous liquid which can be applied at room temperature as a liquid but which forms a semi-solid gel when warmed to body temperature has been utilized as a vehicle for some drug delivery since such a system combines ease of application with greater retention at the site requiring treatment than would be the case if the aqueous composition were not converted to a gel as it is warmed to mammalian body temperature. In U.S. Pat. No. 4,188,373, PLURONIC® polyols are used in aqueous compositions to provide thermally gelling aqueous systems. Adjusting the concentration of the polymer provides the desired sol-gel transition temperature, that is, the lower the concentration of polymer, the higher the sol-gel transition temperature, after crossing a critical concentration minimum, below which a gel will not form.

In U.S. Pat. Nos. 4,474,751 and 4,478,822 drug delivery systems are described which utilize thermosetting gels; the unique feature of these systems is that both the gel transition temperature and/or the rigidity of the gel can be modified by adjusting the pH and/or the ionic strength, as well as by the concentration of the polymer.

Other patents disclosing pharmaceutical compositions which rely upon an aqueous gel composition as a vehicle for the application of the drug are U.S. Pat. Nos. 4,883,660; 4,767,619; 4,511,563; 4,861,760; and 5,318,780. Thermosetting gel systems are also disclosed for application to injured mammalian tissues of the thoracic or peritoneal cavities in U.S. Pat. No. 4,911,926.

Ionic polysaccharides have been used in the application of drugs by controlled release. Such ionic polysaccharides as chitosan or sodium alginate are disclosed as useful in providing spherical agglomerates of water-insoluble drugs in the Journal of Pharmaceutical Sciences, Volume 78, Number 11, November 1989, Bodmeier et al. Calcium alginate gel formulations have also found use as a matrix material for the controlled release of herbicides, as disclosed in the Journal of Controlled Release, (1986), pages 229–233, Pfister et al.

In U.S. Pat. No. 3,640,741, a molded plastic mass composed of the reaction product of a hydrophilic colloid and a crosslinking agent such as a liquid polyol, also containing an organic liquid medium such as glycerin, is disclosed as useful in the controlled release of medication or other additives. The hydrophilic colloid can be carboxymethyl cellulose gum or a natural alginate gum which is cross-linked with a polyol. The cross-linking reaction is accelerated in the presence of aluminum and calcium salts.

In U.S. Pat. No. 4,895,724, compositions are disclosed for the controlled release of pharmacological macromolecular compounds contained in a matrix of chitosan. Chitosan can be cross-linked utilizing aldehydes, epichlorohydrin and benzoquinone.

In U.S. Pat. No. 4,795,642, there are disclosed gelatin-encapsulated, controlled-release compositions for release or pharmaceutical compositions, wherein the gelatin encloses a solid matrix formed by the cation-assisted gellation of a liquid filling composition incorporating a vegetable gum together with a pharmaceutically-active compound. The vegetable gums are disclosed as polysaccharide gums such as alginates which can be gelled utilizing a cationic gelling agent such as an alkaline earth metal cation.

While the prior art is silent with respect to aqueous drug delivery vehicles and isotonicity thereof, osmotic drug delivery systems are disclosed in U.S. Pat. No. 4,439,196 which utilize a multi-chamber compartment for holding osmotic agents, adjuvants, enzymes, drugs, pro-drugs, pesticides, and the like. These materials are enclosed by semipermeable membranes so as to allow the fluids within the chambers to diffuse into the environment into which the osmotic drug delivery system is in contact. The drug delivery device can be sized for oral ingestion, implantation, rectal, vaginal, or ocular insertion for delivery of a drug or other beneficial substance. Since this drug delivery device relies on the permeability of the semipermeable membranes to control the rate of delivery of the drug, the drugs or other pharmaceutical preparations by definition, are not isotonic with mammalian blood.

To date prescription pain and antiinflammatory medications which have been formulated for topical use have not been approved for sale in the United States. This is due to their lack of efficacy and a formulation failure to demonstrate measurable amounts of drug In the blood and urine of patients treated win these preparations. Thus proof of their ability to be transdermally transported through the skin has not been successful.

In contrast, over-the-counter drugs which include counter-irritants such as menthol, eucalyptus, and camphor are sold for mild relief of minor problems. These products are designed to counter-irritation and are not intended for deep penetration of tissue structures below the skin, namely into areas which include joints, ligaments, tendons and cartilage. The over-the-counter drugs described above may be purchased without prescription.

A need thus exists for the administration of active therapeutic agents that can be applied topically and transported through the skin.

SUMMARY OF THE INVENTION

The present invention relates to the formation of a stable, sterile gelled composition and its use in treating acute or chronic conditions. More particularly, this invention relates to a stable, sterilized composition, optionally containing a therapeutic drug, which comprises: a polymer matrix composed of a highly negative charged polymer material which may be selected from the group consisting of polysulfated glucosoglycans, glycosaminoglycans, mucopolysaccharides and mixtures thereof, and a nonionic polymer which may be selected from the group consisting of carboxymethylcellulose sodium, hydroxyethyl cellulose, hydroxypropyl cellulose, and mixtures thereof.

Another embodiment of this invention involves a method for the treatment of a condition in animals, which comprises topically applying therapeutically effective doses of a gelled suspension of a composition comprising an optional drug within a polymer matrix which is suspended in a liquid medium. Preferably, one of the polymer materials has a mean average molecular weight below about 800,000, and the other polymer is a nonionic cellulose derivative. The present invention utilizes a novel combination of polymers each having a specific ionicity. More specifically, the polymers used in the formulation are of two basic types: those which have a strong negative charge, and those which are non-ionic or have no charge attached to them.

An alternative embodiment of the invention involves a process for the use of a composition as a medical device, for drug delivery, the application of a diagnostic agent, or the prevention of post operative adhesions. This process involves topically administering to a mammal an aqueous gelled composition containing a polymer matrix composed of negatively charged polymers blended with nonionic polymers.

An additional embodiment involves the preparation of an antiarthritic gelled composition which comprises an active NSAID drug dispersed within a matrix containing a negative charged polymer having a mean average molecular weight between about 650,000 and 800,000 blended with a nonionic polymer, wherein the molar ratio of the charged polymer to the nonionic polymer is 1:0.5 to 4 and the negative charged polymer is present in amounts of about 2.0% to about 3.0% by weight.

DETAILED DESCRIPTION OF THE INVENTION

It has been unexpectedly discovered that an effective therapeutic level of a drug may be administered topically and transdermally delivered through the skin into various sites where the drug is therapeutically effective. In order for this to be accomplished, it has been discovered that the active drug must be suspended or entrapped in a specially designed polymer matrix containing a specific molar ratio of negatively charged polymers and a non-ionic polymer suspended or dissolved in water and solubilizers.

This system is believed to form a matrix which microencapsulates, suspends, and/or entraps the active drug entity such that when it is administered, it is slowly released into the systemic circulatory system or muscular tissue providing a method of delivering an active drug to an affected site in the body through the skin.

The molar ratio of the polymers present in the matrix is critical in this invention. It has been found that molar ratios the negatively charged polymer to the non-ionic polymer must be from 1:0.5 to 4, and preferably from 1:0.5 to 2.0, and most preferably from 1:0.7 to 2.5. For transdermal delivery of drugs, it has been found that ratios either higher or lower than these levels will result in a polymer shearing effect which produces unacceptable turbulence and air pockets in the composition with resulting loss of potency and efficacy. Furthermore, the solutions tend to separate and form distinct polymer layers when ionic molarity is not appropriate.

At least one of the polymers used to form the matrix of this invention must be sufficiently negatively charged to aid in the dispersion, encapsulation or solubilization of the drug. Particularly preferred polymers which have mean average molecular weights below about 800,000 and preferably molecular weights between 650,000 to 800,000 have been found acceptable to form usable polymer matrixes for transdermal delivery. Polymers with mean average molecular weights between 700,000 and 775,000 are most preferred.

Polymers having molecular weights above about 800,000 form solid gels in solution and are unable to serve as part of a transdermal delivery system. Furthermore, the polymers must be sterilizable and be stable during sterilization so that the polymer does not lose molecular weight once formulated into the final transdermal delivery form.

Exemplary, non-limiting examples of compounds that may he used as a source of this molecular weight polymer include polysulfated glucosoglycans, glycosaminoglycans, and mucopolysaccharides, derivatives thereof and mixtures thereof. Particularly preferred mucopolysaccharides are chondroitin sulfate and hyaluronic acid salts. Exemplary hyaluronate salts include sodium, calcium, potassium and magnesium salts with hyaluronate sodium being most preferred.

Hyaluronic acid (HA) occurs naturally in joint synovial fluid, where it plays a lubricating role, and may have biological activity was well. HA is a mucopolysaccharide, and may alternatively be referred to as glycosaminoglycan. The repeating unit of the hyaluronic acid molecule is a disaccharide consisting of D-glucuronic acid and N-acetyl-D-glucosamine. Because hyaluronic acid possesses a negative charge at neutral pH, it is soluble in water, where it forms highly viscous solutions. The D-glucuronic acid unit and N-acetyl-D-glucosamine unit are bonded through a glycosidic, beta (1-3) linkage, while each disaccharide unit is bonded to the next disaccharide unit through a beta (1-5) linkage. The (beta 1-4) linkages may be broken through hydrolysis with the enzyme hyaluronidase.

A variety of substances, commonly referred to as hyaluronic acid, have been isolated by numerous methods from various tissue sources including umbilical cords, skin, vitreous humour, synovial fluid, tumors, haemolytic streptocci pigskin, rooster combs, and the walls of veins and arteries. It is also being synthesized artificially and by recombinant technology.

Conventional methods for obtaining hyaluronic acid results with a product having differing properties and a wide range of viscosities. U.S. Pat. No. 2,585,546 to Hadian, discloses an example of a method for obtaining hyaluronic acid and which involves extracting acetone-washed umbilical cords with a dilute salt solution, acidifying the resulting extract, removing the clot so formed, precipitating some hyaluronic acid with protein from the acidified extract with ammonium sulfate, agitating the liquid with pyridine, precipitating another fraction highly contaminated with protein, followed by more ammonium sulfate which forces some pyridine out of solution along with the high viscosity hyaluronic acid. The hyaluronic acid collects at the interface between the two liquid phases and may be separated by filtration, centrifugation or another usual procedure. A modification of this process involves the fractionation of the acidic salt extract from umbilical cords with alcohol and ammonium sulfate. Alcohol is added to the acidic salt extract, and the resulting precipitate is removed. Solid ammonium sulfate is added to the liquid until saturation and the solution forms two chases with a precipitate of hyaluronic acid at the interface.

U.S. Pat. No. 4,517,296 to Bracke et al. is directed to the preparation of hyaluronic acid in high yield from Streptococcus bacteria by fermenting the bacteria under anaerobic conditions in a $CO_2$ enriched growth medium, separating the bacteria from the resulting broth and isolating the hyaluronic acid from the remaining constituents of the broth. Separation of the microorganisms from the hyaluronic acid is facilitated by killing the bacteria with trichloroacetic acid. After removal of the bacteria cells and concentration of the higher molecular weight fermentation products, the hyaluronic acid is isolated and purified by precipitation, resuspension and reprecipitation.

One particular fraction of hyaluronic acid (HA) that exhibits excellent matrix formation according to the present invention is hyaluronate sodium having a mean or average molecular weight between 650,000–800,000, preferably 700,000–775,000 with a high degree of purity, 95–105% free, and preferably at least 98% pure, from contamination of related mucopolysaccharides. Furthermore, this hyaluronic acid has a sulphated ash content of less than 15% and a protein content of less than 5%. Examples of usable base salts include those safe from animal and human use, such as sodium, potassium, calcium, and magnesium salts or the like.

In contrast to HA, chondroitins are mucopolysaccharides comprising repeating units of D-glucuronic acid and N-acetyl-D-galactosamine. Chondroitin sulphates are important components of cartilage and bone and are excellent for preparing the polymer matrix herein.

The negative charged polymers are generally present in the system in amounts which enable a solid gel to be formed. Generally, gels are formed using amounts of about 2.0 to about 3.0%. by weight with amounts of about 2.1 to about 2.5% by weight being preferred for use as a topical gel.

The solutions used to prepare the gels of the present invention may be prepared in a variety of ways. For example, the polymers may be dissolved in water and purified either separately or jointly and then the optional active drug added to the system.

A particularly preferred procedure involves separately dissolving the nonionic polymer in water and centrifuging the material to form a solution and remove impurities. This may be conveniently done at rotation speeds of 2000 rpm for times of about 30 minutes to about two hours.

In contrast, the negative charged polymer may be blended and stirred in water until it is dissolved. This Process must be done while avoiding the formation of bubbles and while freeing the polymer of its electrostatic activity. Furthermore, the molecular weight of the polymer must not be significantly changed during processing and as such mild process conditions are required. Processing conditions of 400–3000 rpm for durations of 16–24 hours have been found acceptable to produce stable solutions or gels of the charged polymer.

Conventional pharmaceutically acceptable emulsifiers, suspending agents, antioxidants (such as sodium metabisulfate) and preservatives (such as benzyl alcohol) may then be added to this system. Once all the components are blended together, such as by mixing 400–3000 rpm for one to four hours, the system is filled into tubes and sterilized. The resulting system is a clear gel which is storage stable for several years.

The drug may be added to the homogenous solution or gel separately once dissolved or disbursed in water. Emulsifiers, suspending agents and preservatives may then be added to this system. One particularly nonlimiting effective material for solubilizing water insoluble drugs is methoxypolyethylene glycol (MPEG). Once all the components are blended together, for 400–3000rpm for 1 to 4 hours, the system is filled into tubes and sterilized. The resulting system is storage stable for several years.

The formulations may be used topically and also contain conventional pharmaceutically acceptable excipients well known to those skilled in the art, such as surfactants, suspending agents, emulsifiers osmotic enhancers, extenders and dilutants, pH modifiers as well as fragrances, colors, flavors and other additives.

As indicated above, the active drug agents may be blended with the aqueous polymer matrix at the time of manufacture. As such, the drug when in the form of a water-soluble solid is simply diluted with sterilized water or polymer matrix solution and prepared in gel form.

The dosage system can be formed with or without the use of pharmaceutically acceptable preservatives. A significant advantage of the dosage form of the present system relates to its ability to allow the drug to slowly diffuse through tissue when administered thus allowing for an effective therapeutic dose to be present for many house.

In this regard, it should be noted that reference to therapeutically effective dose does not necessarily relate to conventional dosage levels, but does relate to drug levels that achieve an effective therapeutic level at the dose employed, which may be the same level but not at the same frequency of administration previously required for drugs taken orally or by injection. This not only significantly reduces the number of doses required to achieve the same effect, but it also reduces costs, maintenance and health hazards associated with conventional treatment therapies. Additionally, it results in immediate and continued drug release for long periods of time spanning several hours in duration.

Doses may vary from patient to patient depending on the type and severity of the condition being treated and the drug being administered. Generally, doses of 1 ml to 75 ml may be administered with preferred doses using 2 to 25 ml of the gelled matrix system.

The formulations of this invention may be used to treat a variety or mammal and animal conditions and physical states. These systems have particular application to pain management, namely the treatment and alleviation of pain associated with any disease, condition or physical state.

Without being limited to the specific pain being treated, the preparations of this invention may treat the following nonlimiting locations or sources of pain below the dermal level of the skin, including, but not limited to knees, ankles, hands, feet and neck.

In addition to treating disorders associated with pain below the dermal level of the skin, the preparations of this invention may be used to treat a wide variety of dermatologic disorders. Exemplary, non-limiting disorders include dermatitis conditions such as: Contact Dermatitis; Atopic Dermatitis; Seborrheic Dermatitis; Nummular Dermatitis; Chronic Dermatitis of Hands and Feet; Generalized Exfoliative Dermatitis; Stasis Dermatitis; and Localized Scratch Dermatitis; bacterial infections of the skin, such as: Staphylococcal Diseases of the Skin, Staphylococcal Scalded Skin Syndrome; Erysipelas; Folliculitis; Furuncles; Carbuncles; Hidradenitis Suppurativa; Paronychial Infections and Erythrasma; superficial fungal infections such as: Dermatopyte Infections; Yeast Infections; Candidiasis; and Tinea Versicolor; parasitic infections of the skin such as: Scabies; Pediculosis; and Creeping Eruption; disorders of hair follicles and sebaceous glands such as: Acne; Rosacea; Perioral Dematitis; Hypertrichosis; Alopecia; Pseudofolliculitis Barbae; and Keratinous Cyst; scaling papular diseases, such as: Psoriasis; Pityriasis Rosea; and Lichen Planus; pressure sores; benign tumors and malignant tumors.

A particularly preferred disorder to be treated are pressure sores. Factors that precipitate pressure sores include loss of pain and pressure sensations (which ordinarily prompt the patient to shift position and relieve the pressure) and the thinness of fat and muscle padding between bony weight-bearing prominences and the skin. Disuse atrophy, malnutrition, anemia, and infection play contributory roles. In a paralyzed extremity, loss of vasomotor control leads to a lowering of one in the vascular bed and a lowered circulatory rate. Spasticity, especially in patients with spinal cord injuries, can place a shearing force on the blood vessels to further compromise circulation.

The most important of the extrinsic factors is pressure. Its force and duration directly determine the extent of the ulcer. Pressure severe enough to impair local circulation can occur within hours in an immobilized patient, causing local tissue anoxia that progresses, if unrelieved, to necrosis of the skin and subcutaneous tissues. The pressure is due to infrequent shifting of the patient's position; friction and irritation from ill-adjusted supports or wrinkled bedding or clothing may be contributory. Moisture, which may result from perspiration or from urinary or fecal incontinence, leads to tissue maceration and predisposes to pressure sores.

The stages of decubitus ulcer formation correspond to tissue layers. Stage 1 consists of skin redness that blanches or disappears on pressure; the skin and underlying tissues are still soft. Stage 2 shows redness, edema, and induration, at times with epidermal blistering or desquamation. In stage 3, the skin becomes necrotic with exposure of fat and drainage from the wound in stage 4, necrosis extends through the skin and fat to muscle; further fat and muscle necrosis characterizes stage 5. In stage 6, bone destruction begins, with periostitis and osteitis, progressing finally to osteomyelitis, with the possibility of septic arthritis, pathologic fraction and septicemia.

The best known treatment for pressure sores is prevention. Pressure on sensitive areas must be relieved. Unless a full flotation bed (water bed) is used to provide even distribution of the patient's weight through hydrostatic buoyancy, the bedridden patient's position must be changed at least once ever 2 hours until tolerance for longer periods can be demonstrated (by the absence of redness) . Air-filled alternating-pressure mattresses, sponge-rubber "egg-crate" mattresses, and silicone gel or water mattresses decrease pressure on sensitive areas but do not negate the need for positon changes. A turning (Stryker) frame facilitates turning patients with cord injuries. Protective padding (eg, sheepskin or a synthetic equivalent) at bony prominences should be used under braces or plaster casts, and at potential pressure sites a window should be cut out of the cast. A wheelchair patient must be able to shift his position every 10 to 15 minutes even if he is using a pressure-relieving pillow. Otherwise, patients in chairs may be more likely to have pressure sores than those who are in bed.

The major problem in treating decubitus ulcer is that the ulcer is like an iceberg, a small visible surface with an extensive unknown base, and to date there is no good method to determine the extent of tissue damage. Ulcers that have not advanced beyond stage 3 may heal spontaneously if the pressure is removed and the area is small.

Stage 4 ulcers require debridement; some may also require deeper surgery. When the ulcers are filled with pus and necrotic debris, application of dextranomer beads or other and newer hydrophilic polymers may hasten debridement without surgery. Conservative debridement of necrotic tissue with forceps and scissors should be instituted. Some debridement may be done by cleansing the wound with 1.5 % hydrogen peroxide. Wet dressings of water (especially whirlpool baths) will assist in debriding. The granulation that follows removal of necrotic tissue may be satisfactory for skin grafts to cover small areas.

More advanced ulcers with fat and muscle involvement require surgical debridement and closure. Affected bone tissue requires surgical removal; disarticulation of a joint may be needed. A sliding full-thickness skin flap graft is the closure of choice, especially over large bony prominences (eg, the trochanters, ischia, and sacrum), since scar tissue cannot develop the tolerance to pressure that is needed.

For spreading cellulitis, a penicillinase-resistant penicillin or a cephalosporin is necessary.

Many new dressings and topical agents are being tested and made available for use. No one powder, gel, or dressing is universally superior. The subject is complex; ie, some are wet and lead to Pseudomonas infection if used too long, others are painful, all are expensive, and some are of little value.

Use of the present formulations either atone or in combination with various therapeutic agents overcomes all of these prior art deficiencies.

It has also been unexpectedly found that when the system is administered in a repetitive manner, once the effects of the active drug are reduced in intensity or effectiveness, such repeat treatments may result in a synergistic effect by enhancing the initial term of relief to a period which exceeds the initial time of relief. This is also experienced on subsequent treatments. In this way, the present formulations are able to extend relief or treatment from normally several hours to at least several days of relief. The use of repeat applications enhances drug release which significantly reduces drug dependence. It also results in the relief of continued tissue damage and may even assist in tissue repair.

Regardless of the route of administration elected, the formulations of the present invention are formulated into pharmaceutically acceptable dosage forms by conventional methods known in the pharmaceutical art.

As discussed above, an effective but nontoxic amount of the system is employed in treatment. The dose regimen for administering drugs or treating various conditions, such as pair as described above, is selected in accordance with a variety of factors including the type, age, weight, sex, and medical condition of the subject, the severity of the pain, the route or administration and the particular complex or combination of drugs employed. Determination of the proper dose for a particular situation is within the skill of the art. Generally, treatment is initiated with smaller dosages which are less than the optimum doses of the compound. Thereafter, the dose is increased by small increments until the optimum effect under the circumstances is reached. For convenience, the total daily dosage may be divided and administered in portions during the day if desired. Generally, amounts of drug may vary from 0.0001% to about 75% by weight of the system when using topically with 2 to 25 ml concentrations and preferably in 3 to 10 ml amounts.

The formulations of this invention are particularly useful in the administration of drugs that could be previously administered only orally.

The importance of this invention becomes apparent when one considers the side-effects associated with conventional, oral drugs for treating osteoarthritis, including NSAIDs such as diclofenac.

Typically, NSAIDs have been known to produce gastric and intestinal irritation. In addition, scarring and ulceration of the intestinal tract is quite common in patients on short- or long-term NSAID therapy. Unfortunately, there do not appear to be many alternatives to NSAID therapy, for patients suffering from extremely painful, inflammatory conditions which may include osteoarthritis and other inflammatory disorders. Thus, new NSAIDs are constantly entering the market place, each one, however, with the same potential to cause unpleasant and often serious side-effects.

The transdermal applications of NSAIDs and particularly diclofenac described herein, are a much safer way of treating inflammatory disorders including those related to osteoarthritis also known as Degenerative Joint Disease (DJD).

When a person takes an oral form of diclofenac, typically 100 mg to 150 mg per day, the drug must be circulated through systemic blood and only a small amount ends up in the specific site that is intended for treatment, such as the knee. Individuals with osteoarthritis are generally treated with NSAIDs including, but not limited to, diclofenac, ibuprofen, Aspirin, etc., which as previously mentioned produce an antiinflammatory effect at the joint level. At therapeutic dosages for diclofenac which are usually between 100 mg and 200 mg per day, more than 50% of all treated patients will experience some form of GI (gastrointestinal) distress.

The transdermal delivery system described herein offers a major alternative especially for those individuals who have a history of undesirable side-effects associated with gastric and intestinal irritation. Also for those patients who have already suffered damage, including ulceration and loss of absorption from the intestinal tract, the transdermal preparations described herein present a new way of providing effective treatment and relief of painful symptoms. It has become a common practice of rheumatologists and other specialists treating osteoarthritic and associated disorders to use ulcer-type drugs of the H2 blocking variety including, but not limited to ranitidine (Zantac), Pepsid and cimetidine (Tagamet) by Smith Kline. The addition of these drugs to already high regimens "(polypharmacy)" of therapeutic agents is not desirable since these drugs often produce their own undesirable side-effects. Although an occasional patient will experience mild stomach upset from the transdermal preparation described herein, the effect is transient and of mild severity. In addition, patients treated with the present transdermal diclofenac, find that they can function for longer periods of time (4 to 6 hours) and can simply apply more of the therapeutic gel to maintain a continuous reduction in pain and inflammation. In this way, patients who apply the drug topically 3 to 4 times a day can experience sustained around-the-clock relief.

Several attempts have been made in the past to produce effective transdermal preparations. These preparations have not been approved in North America for some drugs, like diclofenac, by the regulatory authorities as of this time. Some of the reasons cited are lack of proven transdermal delivery. In the case of the current invention, transdermal delivery can be substantiated by:

1. Measurable blood levels of diclofenac.
2. Diclofenac presence in the urine of patients treated with the transdermal drug.
3. The presence of diclofenac in synovial fluid where joints with synovial fluid are the target sites for treatment.
4. Rapid absorption following topical administration.
5. Rapid relief of painful symptoms in a significant number of patients already being treated with the products.

In Europe, Voltaren cream (Ciba-Geigy) is Popular for the treatment of osteoarthritic conditions. This preparation contains diclofenac sodium. However, the manufacturers have not demonstrated to the satisfaction of North American regulators proven ability for the cream to be transdermally absorbed. Amounts of diclofenac delivered by the cream are considered to be minimal at best.

It should be pointed out that diclofenac, as the sodium or potassium salt, is a benzeneacetic acid derivative, designated chemically as 2-[2,6-di-chlorophenyl)amino] benzeneacetic acid, monosodium or monopotassium salt. It is freely soluble in methanol, soluble in ethanol, and practically insoluble in chloroform and in dilute acid. Diclofenac sodium is sparingly soluble in water while diclofenac potassium is soluble in water. Diclofenac, the anion in Voltaren® and Calaflam®, is a nonsteroidal anti-inflammatory drug (NSAID). In pharmacologic studies, diclofenac has shown anti-inflammatory, analgesic, and antipyretic activity. As with other NSAIDs, its mode of action is not known; its ability to inhibit prostaglandin synthesis, however, may be involved in its anti-inflammatory activity, as well as contribute to its efficacy in relieving pain related to inflammation and primary dysmenorrhea. With regard to its analgesic effect, diclofenac is not a narcotic.

The current invention represents a break-through in that for the first time measurable, detectable levels of diclofenac can be delivered to affected sites. For those patients who experience mild intestinal discomfort following administration, it is recommended that the transdermal gel preparation described herein, be administered after meals.

In addition to the negatively charged polymers, the transdermal polymer matrix must contain a non-ionic polymer which facilitates in retarding the absorption of the active drug through the skin and delays or slows down in animals natural absorption of the negatively charged polymer.

Without the presence of this component, the active drug would not be delivered transdermally into the site targeted for treatment at levels which are therapeutically effective. In addition to the non-ionic polymers described in this system, these materials are necessary to provide thorough penetration of skin layers including the epidermis, dermis and fatty tissue layers. Evidence of this absorption through the skin layers and into the capillary bed and ultimately the systemic system is evidenced by the fact that detectable, measurable blood levels of active drug, such as diclofenac, can be found in the urine of patients treated with the diclofenac transdermal preparation described herein.

Particularly preferred nonionic polymers are cellulose derivatives and particularly those selected from the group consisting of carboxymethylcellulose sodium, hydroxyethyl cellulose, hydroxypropyl cellulose and mixtures thereof. These particular polymers have been found to possess exceptional ability to form sustained release matrix formulations when used in combination with a negatively charged polymer. Such polymers are generally employed in amounts of about 0.1% to about 1.5% and preferably about 0.5 to about 1.4%. Amounts above about 1.5% result in the formation of a solid gel when used with the negatively charged polymer. Amounts below about 0.1% have not been found suitable to prepare a storage stable product that has sustained drug release.

A particularly preferred HEC concentration is about 0.2% to about 1.0% by weight of the matrix.

A wide variety of medicaments which may be administered topically may be used in the delivery system according to this invention. These include drugs from all major categories, and without limitation, for example, anesthetics including benzocaine, tetracaine, mepivacalne, prilocaine, etidocaine, bupivacaine and lidocaine; analgesics, such as acetaminophen, ibuprofen, fluriprofen, ketoprofen, voltaren (U.S. Pat. No. 3,652,762), phenacetin and salicylamide; nonsteroidal anti-inflammatories (NSAIDS) selected from the group consisting of naproxen, acetaminophen, ibuprofen, flurbiprofen, ketoprofen, phenacetin, salicylamide, and indomethacin; antibiotics including amebicides, broad and medium spectrum, fungal medications, monobactams and viral agents and specifically including such as erythromycin, penicillin and cephalosporins and thier derivatives; central nervous system drugs such as thioridazine, diazepam, meclizine, ergoloid mesylates, chlorpromazine, carbidopa and levodopa; metal salts such as potassium chloride and lithium carbonate; minerals selected from the group consisting of iron, chromium, molybdenum and potassium; immunomodulators; immunosuppressives; thyroid preparations such as synthetic thyroid hormone, and thyroxine sodium; steroids and hormones including ACTH, anabolics, androgen and estrogen combinations, androgens, corticoids and analgesics, estrogens, glucocorticoid, gonadotropin, gonadotroc-n releasing, human growth hormone, hypocalcemic, menotropins, parathyroid, progesterone, progestogen, progestogen and estrogen combinations, somatostatis-like compounds, urofollitropin, vasopressin, and others; and vitamins selected from water-soluble vitamins such as B complex, vitamin C, vitamin B12 and folic acid and veterinary formulations.

One particular criteria of the drug is that they must be solubilized in the polymer matrix solution in order to be topically administered.

A particularly preferred additional use of the compositions of this invention include their uses as 1) a medical device, 2) for drug delivery, 3) the application of a diagnostic agent or 4) the prevention of post operative adhesions.

The following examples are illustrative of preferred embodiments of the invention and are not to be construed as limiting the invention thereto. All polymer molecular weights are mean average molecular weights. All percentages are based on the percent by weight of the final delivery system or formulation prepared unless otherwise indicated and all totals equal 100% by weight.

EXAMPLE 1

This example demonstrates the formation of a transdermal nonsteroidal antiinflammatory preparation known as diclofenac which produces relief of osteoarthritic and associated pain in areas affected by the disease. Such areas include, but are no limited to, knees, ankles, feet, back, neck, elbows, and hips.

Example 1 also demonstrates the formation of a transdermal preparation containing the NSAID drug when administered topically to sites affected by rheumatic or osteoarthritic disease will have an analgesic and beneficial effect. The onset of this beneficial effect in the form of pain relief and reduction of inflammation occurs between 10 and 20 minutes following topical administration and lasts for up to 6 hours.

The dosage range for the drug is between 2–4 ml (60 mg–120 mg) depending on the severity and site of the affected area.

| MATERIALS | |
|---|---|
| Diclofenac sodium | 3% |
| Sodium hyaluronate (HA) | 2.3% |
| Hydroxyethyl cellulose (HEC) | 0.7% |
| Methoxypolyethylene glycol (MPEG) | 10% |

-continued

| MATERIALS | |
|---|---|
| Benzyl alcohol | 2.5% |
| Water | Remainder |

BATCH SIZE 1500 ml

1. Into a sterilized glass vessel is added 1062.5 ml of sterile water which is stirred at 1500 to 2000 rpm. Slowly add 34.5 grams of HA, having a molecular weight of around 700,000 to 775,000 and a purity described above. Allow to stir for 16 to 20 hours until all of the HA polymer has dissolved into the water and a crystal-clear viscous solution has formed.
2. Prepare a 0.7% solution of HEC by adding 10.5 grams of the solid material under aseptic conditions to 250 ml of sterile water. Allow to dissolve for 1 to 2 hours while stirring at 1500 to 2000 rpm. Add the HEC solution go the HA solution and mix for 10 to 15 hours until a homogeneous solution is produced.
3. Carefully measure 150 ml of methoxypolyethylene glycol (MPEG) 10% into the mixture. RPM speeds should be increased for the mixture while this step is being performed to 2500 rpm. The resulting mixture thus formed should be allowed to mix at 2000 rpm for an additional 3 to 4 hours.
4. At this point 2.5% of benzol alcohol or 37.5 ml is added to the mixture. Again, the rpm speed is increased during this part of the procedure to 2500. The mixture should be allowed to mix for 3 to 5 hours at 2000 rpm.
5. Using safe techniques, 45 grams (3%) of the diclofenac should be slowly added to the mixture. Again the rpm speed for the purpose of addition of diclofenac should be increased to 2500, and the entire 45 grams of diclofenac should be completed within 15 minutes.

The final mixture is clear with a slight green tint following 15 to 20 hours of further mixing at 2000 rpm. The final product should be transferred, using aseptic technics, to 25 ml borasylicate glass jars with a lined cap.

EXAMPLE 2

The formula and method of manufacture of Example 1 is repeated for diclofenac potassium. The only difference is that MPEG is not used.

| MATERIALS | |
|---|---|
| Diclofenac potassium | 3% |
| Sodium hyaluronate (HA) | 2.3% |
| Hydroxyethyl cellulose (HEC) | 0.7% |
| Benzyl alcohol | 2.5% |

1. Into a sterilized glass vessel is added 1062.5 ml of sterile water which is stirred at 1500 to 2000 rpm. Slowly add 34.5 grams of HA, having a molecular weight of around 700,000 to 775,000 and a purity described previously. Allow to stir for 16 to 20 hours until all of the HA polymer has dissolved into the water and a crystal-clear viscous solution has formed.
2. Prepare a 0.7% solution of HEC by adding 10.5 grams of the solid material under aseptic conditions to 250 ml of sterile water. Allow to dissolve for 1 to 2 hours while stirring at 1500 to 2000 rpm. Add the HEC solution to the HA solution and mix for 10 to 15 hours until a homogeneous solution is produced.
3. At this point 2.5% of benzol alcohol or 37.5 ml is added to the mixture. Again, the rpm speed is increased during this part of the procedure to 2500. The mixture should be allowed to mix for 3 to 5 hours at 2000 rpm.

4. As described above, using safe techniques, 45 grams (3%) of the diclofenac is slowly added to the mixture. Again the rpm speed for the purpose of addition of diclofenac should be increased to 2500, and the entire 45 grams of diclofenac should be completed within 15 minutes.

The final mixture is clear with a slight green tint following 15 to 20 house of further mixing at 2000 rpm.

The final product should be transferred, using aseptic technic, to 25 ml borasylicate glass jars with a lined cap.

EXAMPLE 3

The general manufacturing procedure of Example 1 is repeated for a topical dermalogical preparation. The main difference in composition is the use of methylparabin as a preservative.

| MATERIALS | |
|---|---|
| Sodium hyaluronate (HA) | 2.5% |
| Hydroxyethyl cellulose (HEC) | 1.25% |
| Benzyl alcohol | 1% |
| Methyl parabin | 0.2% |
| Water | Q.S. |

Prior to dissolving the HA into the water, methyl parabin is dissolved and then HA added thereto. The remaining process steps of Example 1 were then repeated.

When 3 to 5 milliliters of this formulation was applied to pressure sores 3 to 4 times daily, the tissue healed and returned to a normal condition within 4 to 7 days.

TEST PROCEDURE I

Patient LHN's complaint is of headache and pain in the back of the neck.
History:
She has been getting headaches for 30 years since she was 5-years-old. She has had several injuries in the past including being thrown down the stairs.

In 1996, it was noted that the headaches were bifrontal, sometimes behind the eyes and also in the sides of the head and in the parietal region. They were often associated with nausea and vomiting.

In June 1996, her headache was frontal, occipital and in the left shoulder going down the left arm, and she also had low back ache.
Physical Examination:
She was tender over the right cervical facets at 2-3, 4-5 and 5-6 and on the left at 2-3 and the greater occipital nerve bilaterally
Diagnosis:
Cervicogenic Headaches.
This was confirmed by diagnostic blocks bilaterally at 2-3, 3-4 and 4-5 which reduced her head and neck pain respectively of 6/10 and 10/10 to 0/10.
Treatment With Diclofenac Gel:
This was rubbed on the facet joint areas of the cervical spine bilaterally. The patient noticed marked decrease of pain in the neck 4 to 8 hours after use.

When the gel was used 2 to 3 times daily, the generalized neck ache was markedly reduced. In addition, some of her headaches were also decreased. It was noted that there was no skin irritation with the use of the gel.

TEST PROCEDURE II

This is a 32-year-old man who complains of headaches.
History:
He complains of headaches in the right upper neck radiating to the right parietal region, the right eye, the right temporal region. They are aching and stabbing with a severity between 6–10/10. They are always present but the severity varies. They have occurred since he had a motor vehicle accident in August 1993.
Physical Examination:
Flexion normal, extension 80%, rotation right 90% and rotation left 90%. He is tender at the cervical facets of right 2-3, left 2-3 and the right lesser occipital nerve.
Diagnosis:
Cervicogenic Headache.
This was confirmed by a positive response to diagnostic facet blocks at the right 2-3 and 3-4 cervical facets.
Treatment With Diclofenac Gel:
This was rubbed on the facet joint area on the right side of the neck and the patient noticed a marked decrease in pain for the next 4 to 8 hours after use. When the gel was used 2 or 3 times a day, the generalized neck ache was markedly reduced. In addition, some of his headaches were also decreased.

TEST PROCEDURE III

Her complaint is of severe holo-cranial headaches.
History:
She gave a history that one and one-half years ago she fell flat on her back on concrete. She has had severe headaches since then although earlier in her life she had headaches that were attributed to migraine.

She is 37-years-old. The headaches are biparietal, temporal, behind the eyes and alter in the day they become bioccipital. They have an aching and throbbing character. Sometimes she wakes up with a headache.

She has had some success with Fiorinal C½ in treating her headaches.
Physical Examination:
Neck: Flexion 30%, extension 40%, right rotation 80% and left rotation 70%. Tenderness of the cervical facets, right 2-3 and 3-4 and left 2-3, 3-4, 4-5 and 5-6, 1+at each.
Diagnosis:
1. Cervicogenic headache.
2. Possible pre-existing migraine.
Treatment With Diclofenac Gel:
This was rubbed on the facet joint areas bilaterally in the neck region. The patient noticed a marked decrease in pain in the neck for 4 to 8 hours after use. When the gel was used 2 to 3 times a day, the generalized neck pain was markedly reduced. In addition, some of her headaches were also decreased.

TEST PROCEDURE IV

This 52-year-old lady had a long history of:
1. Occasional-headaches.
2. Occasional neck pain.
History:
The patient had a long history of headaches of about 30 years duration. These were of a migrainous nature usually on the right side. More recently, these have been associated with neck pain.
Physical Examination:
This revealed a tilt o the head to the left. With the right shoulder higher than the left.

The facet joints at C2-3, C3-4, C4-5 and C5-6 bilaterally were very tender. However, they were particularly tender at C2-3 and C4-5 on the right.
Diagnosis:
Degenerative joint disease of the cervical spine causing chronic headaches and occasional neck aches.
Results of Treatment With Diclofenac Gel:
This was used on three occasions for the neck pain. In each case, it decreased the neck pain substantially. On two occasions, it aborted a migraine headache in its early stages.

TEST PROCEDURE V

This 47-year-old lady has a long history of:
1. Constant headaches.
2. Constant neck aches.
History:
The patient has a history of 7 motor vehicle accidents. She underwent facet rhizolysis about three years ago. This almost entirely relieved her headaches. She still however continued to have neck aches with physical activity particularly involving the neck.
Physical Examination:
This showed some limitation of flexion and extension to about 65% of normal. The facet joints from C2 to C6 were exquisitely tender more on the right than the left.
Diagnosis:
Degenerative joint disease of the cervical spine causing occasional headaches and neck aches.
Treatment With Diclofenac Gel:
The diclofenac gel has successfully relieved her neck ache on three different occasions. Each time the pain relief was almost 100%. In addition, it stopped the beginnings of a headache on each occasion.

TEST PROCEDURE VI

This 26-year-old lady has a long history of:
1. Constant neck ache.
2. Almost daily headaches.
History:
The patient was thrown off a friend's shoulders while playing at a party. She landed on her jaw and had her neck thrust backwards violently.
She was thought to have actually broken her jaw at the time of the fall.
She has been investigated for TMJ disorder because there is clearly some asymmetry in her face since the accident. However, the TMJ specialist felt that there was no TMJ damage that could be found.
She also was found to have tender facet joints from C2 to C6 bilaterally, and she said with her neck thrust forward and with difficulty in flexion and extension particularly extension being only about 60% of normal.

Physical Examination:
This revealed tenderness over the facet joints at C2-3, C3-4, C4-5 and C5-6 bilaterally but especially on the right. And the facet joints were more prominent on the right.
The TMJ was not especially tender to palpation.
Diagnosis:
Degenerative joint disease of the cervical spine causing chronic neck aches and headaches.
Treatment With Diclofenac Gel:
This was used on three occasions for severe neck pain. It decreased the neck pain by about 50%. It did not however relieve the headaches. The patient is now using the gel daily because she does find that it cuts down her neck pain, and she is hoping it will cut down the headaches.

The invention being thus described, it will be obvious that the same may be varied in many ways. Such variations are not to be regarded as a departure from the spirit and scope of the invention and all such modifications are intended to be included within the scope of the following claims.

What is claimed is:

1. A process for the use of a composition as a medical device, for drug delivery, the application of a diagnostic agent, or the prevention of post operative adhesions, said process comprises topically administering to a mammal an aqueous based gelled composition containing a polymer matrix composed of a negatively charged polymer material blended with a nonionic polymer;

wherein the negatively charged polymer material is hyaluronate sodium salt; and wherein the hyaluronate sodium salt has a weight average molecular weight from about 650,000 to about 800,000, a sulphated ash content below about 15%, a protein content below about 5% and purity of at least 98%.

2. The process of claim 1, wherein the negatively charged polymer material is selected from the group consisting of glucosminoglycans, mucopolysaccharides and mixtures thereof.

3. The process of claim 1, wherein the negatively charged polymer material has a weight average molecular weight below about 800,000.

4. The process of claim 1, wherein the negatively charged polymer material has a weight average molecular weight between 700,000 and 775,000.

5. The process of claim 1, wherein the nonionic polymer is selected from the group consisting of carboyxmethylcellulose sodium, hydroxyethyl cellulose, hydroxypropyl cellulose and mixtures thereof.

6. The process of claim 1, wherein the composition also contains an active therapeutic agent or drug.

* * * * *

UNITED STATES PATENT AND TRADEMARK OFFICE
CERTIFICATE OF CORRECTION

PATENT NO.    : 6,387,407 B1                                         Page 1 of 1
DATED         : May 14, 2002
INVENTOR(S)   : Alan Drizen, Peter Rothbart and Gary M. Nath It is certified that error appears in the above-identified patent and that said Letters Patent is hereby corrected as shown below:

<u>Title page,</u>
Item [63], please delete the phrase "Continuation-in-part of application No. 08/536,750, filed on Sep. 29, 1995, now abandoned", and insert the phrase, "Divisional of application No. 08/796,578, filed on February 6, 1997, now Patent No. 5,897,880, which is continuation-in-part of application No. 08/536,750, filed on Sep. 29, 1995, now abandoned."

Signed and Sealed this

Tenth Day of September, 2002

*Attest:*

*Attesting Officer*

JAMES E. ROGAN
*Director of the United States Patent and Trademark Office*